(12) United States Patent
Hay

(10) Patent No.: US 10,945,860 B2
(45) Date of Patent: Mar. 16, 2021

(54) BIOLOGIC PREPARATION AND DELIVERY SYSTEM

(71) Applicant: James Scott Hay, Parkland, FL (US)

(72) Inventor: James Scott Hay, Parkland, FL (US)

( * ) Notice: Subject to any disclaimer, the term of this patent is extended or adjusted under 35 U.S.C. 154(b) by 164 days.

(21) Appl. No.: 16/389,246

(22) Filed: Apr. 19, 2019

(65) Prior Publication Data

US 2020/0330242 A1    Oct. 22, 2020

(51) Int. Cl.
  *A61F 2/46*      (2006.01)
  *A61B 17/88*     (2006.01)
  *A61F 2/28*      (2006.01)

(52) U.S. Cl.
  CPC ........ *A61F 2/4601* (2013.01); *A61B 17/8805* (2013.01); *A61F 2/2846* (2013.01)

(58) Field of Classification Search
  CPC ... A61F 2/4601; A61F 2/2846; A61B 17/8805
  See application file for complete search history.

(56) References Cited

U.S. PATENT DOCUMENTS

| | | | |
|---|---|---|---|
| 2,316,095 A | 4/1943 | Mead | |
| 4,277,184 A | 7/1981 | Solomon | |
| 4,769,011 A * | 9/1988 | Swaniger | A61F 2/4601 604/218 |
| 5,957,166 A * | 9/1999 | Safabash | B01F 11/0082 141/100 |
| 6,439,439 B1 | 8/2002 | Rickard et al. | |
| 8,628,536 B2 | 1/2014 | Walker et al. | |
| 8,945,137 B1 | 2/2015 | Greenhalgh et al. | |
| 9,173,694 B2 | 11/2015 | Kleiner | |
| 9,370,389 B2 | 6/2016 | Jones et al. | |
| 9,655,748 B2 | 5/2017 | Greenhalgh et al. | |
| 9,668,881 B1 | 6/2017 | Greenhalgh et al. | |
| 10,123,849 B2 | 11/2018 | Greenhalgh et al. | |
| 10,292,747 B2 | 5/2019 | Greenhalgh et al. | |
| 10,405,905 B2 | 9/2019 | Greenhalgh et al. | |
| 2005/0113762 A1 * | 5/2005 | Kay | A61F 2/4601 604/181 |
| 2006/0149282 A1 | 7/2006 | Vendrely et al. | |
| 2007/0198086 A1 * | 8/2007 | Kuroda | A61F 2/4601 623/11.11 |
| 2008/0281336 A1 | 11/2008 | Zergiebel | |
| 2009/0093818 A1 * | 4/2009 | Baroud | A61F 2/4601 606/93 |
| 2009/0204120 A1 * | 8/2009 | Trosken | A61B 17/8816 606/93 |
| 2013/0131683 A1 | 5/2013 | Shah et al. | |
| 2013/0184822 A1 * | 7/2013 | Kleiner | A61F 2/4455 623/17.12 |

(Continued)

*Primary Examiner* — Christian A Sevilla
(74) *Attorney, Agent, or Firm* — Nicholas R. Lewis, P.A.

(57) ABSTRACT

A medical compound preparation and delivery system, including a delivery device, the device including a depressible trigger operably coupled to move a plunger; a cartridge releasably coupled to the delivery device, the cartridge defining a lumen therethrough to receive at least a portion of the plunger therein; a receptacle defining a cavity therein for receiving a medical compound; a first tube slidably positionable within the cavity of the receptacle; and a second tube slidably positionable within the first tube, wherein the cartridge is slidably positionable within the second tube.

20 Claims, 13 Drawing Sheets

(56) References Cited

U.S. PATENT DOCUMENTS

| | | | |
|---|---|---|---|
| 2014/0276572 A1* | 9/2014 | Auyoung | A61B 17/8855 604/506 |
| 2017/0266382 A1* | 9/2017 | Dewey | A61B 17/8811 |
| 2018/0133027 A1* | 5/2018 | Heald | A61B 17/8819 |

* cited by examiner

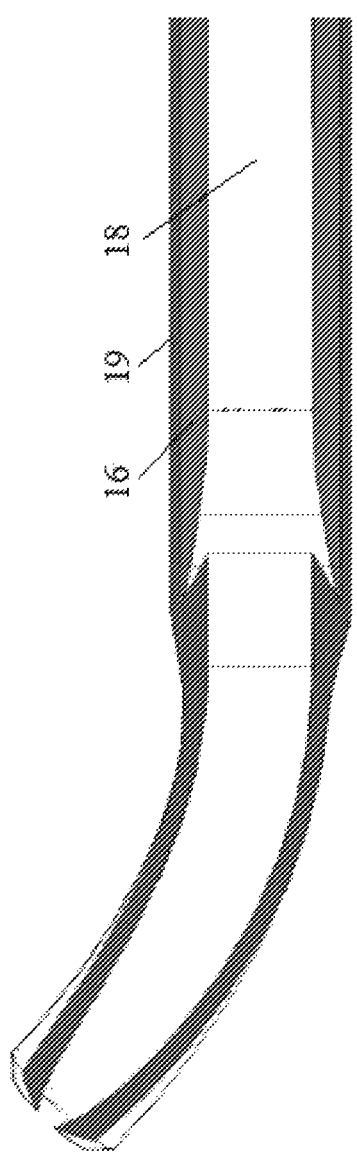
FIG. 5c
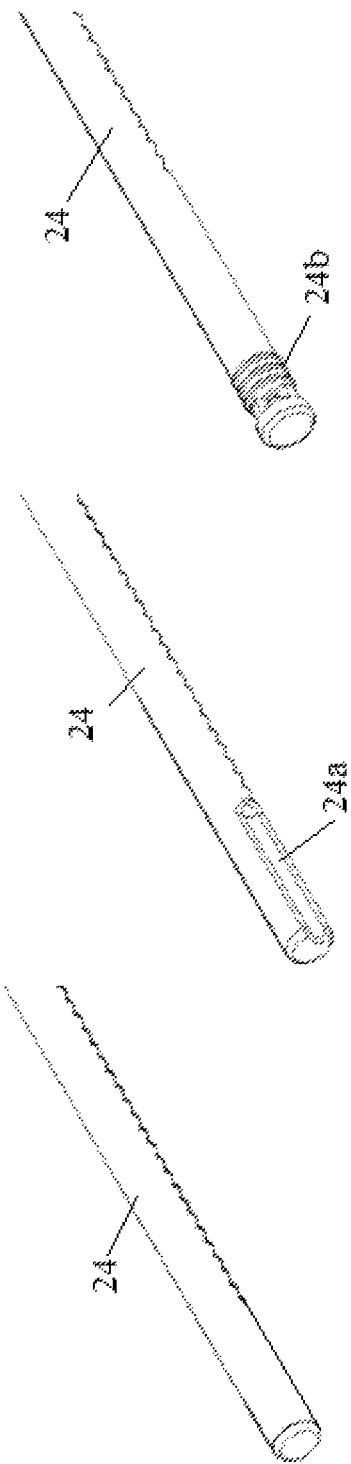
FIG. 6c
FIG. 6b
FIG. 6a

BIOLOGIC PREPARATION AND DELIVERY SYSTEM

CROSS-REFERENCE TO RELATED APPLICATION n/a

STATEMENT REGARDING FEDERALLY SPONSORED RESEARCH OR DEVELOPMENT n/a

FIELD OF THE INVENTION

The present disclosure relates to methods and systems for preparing and controllably delivering biological, pharmaceutical, and/or other therapeutic or healing materials to a surgical site.

BACKGROUND OF THE INVENTION

In many orthopedic procedures, bone graft material is processed and delivered to a surgical site in order to augment the natural bone. Such graft material typically includes autogenous bone, allograft, xenograft, or synthetic bone graft substitutes. In many orthopedic surgical procedures, particularly joint replacement surgery, certain implantable components must be affixed to bone. A patient's bone quality in an area where a prosthetic component is to be implanted must be sufficient to enable effective anchoring of the prosthesis to the bone. In such situations, bone graft material is used to augment the bone. In the case of bone defects or injury, synthetic or natural bone grafts may also be implemented to fix the defect or injury. For example, bone graft materials and methods are used in cavities resulting from tumor removal or significant fractures.

Bone graft procedures are also typically implemented when removing and/or replacing a previously-implanted prosthesis. In such implant revision surgery, a previously implanted prosthesis is removed and replaced with a new prosthesis, and bone graft is used to fill-in or otherwise augment the cavity formed by removal of the previously implanted prosthesis (and any old bone cement, particulate debris, membrane, beads and other remnants associated with the prosthesis) to facilitate secure and desired positioning and implantation of the new prosthesis.

Bone graft may be used in a wet or slurry form, or alternatively, in a dry or particulate/granule form. Moreover, bone graft material may include a range of irregular particle sizes. The present disclosure provides improved systems and methods of use thereof to load and deliver bone graft of varying particulate dimensions in a timely and controlled manner to a particular receiving location.

SUMMARY OF THE INVENTION

The present disclosure advantageously provides a medical compound preparation and delivery system, including a delivery device, the device including a depressible trigger operably coupled to move a plunger; a cartridge releasably coupled to the delivery device, the cartridge defining a lumen therethrough to receive at least a portion of the plunger therein; a receptacle defining a cavity therein for receiving a medical compound; a first tube slidably positionable within the cavity of the receptacle; and a second tube slidably positionable within the first tube, wherein the cartridge is slidably positionable within the second tube. The cavity of the receptacle may be substantially cylindrical and/or may extend entirely through the receptacle. The system may include a base removably coupled to the receptacle to cover a portion of the cavity. The cartridge may define an elongated substantially tubular body. The cartridge may include an arcuate tip. The delivery device may include a ratchet mechanism engageable with the plunger. The delivery device may include a locking element configured to secure the cartridge to the delivery device. The cavity of the receptacle may have a volume between approximately 2 cc and approximately 20 cc. The lumen of the cartridge may define a volume between approximately 2 cc and approximately 20 cc. The dispensing element may define a groove at a distal end thereof to facilitate the collection and/or release of gas or air from the cartridge. The dispensing element may include a sealing element at a distal end thereof. Each of the cartridge, first tube, and second tube may define a tapered end. The system may include a base that is releasably engageable with the receptacle and/or a cap that is releasably engageable with the base. The cap may define one or more vents therein. The system may include a distal tip accessory that defines a curved spout, wherein the distal tip accessory is releasably engageable with the delivery device to substantially enclose the cartridge therein.

A method of preparing a medical compound for delivery is provided, including placing a medical compound into a cavity of a receptacle; slidably positioning a first tube into the cavity such that the medical compound is moved into the first tube; slidably positioning a second tube into the first tube such that the medical compound is moved into the second tube; slidably positioning a cartridge into the second tube such that the medical compound is moved into the cartridge; and releasably securing the cartridge to a delivery device, wherein the delivery device includes a depressible trigger operably coupled to move a plunger into the cartridge to controllably dispense the medical compound from the cartridge. The medical compound may include bone graft. The receptacle may include a substantially cylindrical body. The delivery device may include a ratchet mechanism engageable with the plunger. The delivery device may include a locking element configured to secure the cartridge to the delivery device.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIGS. 5a-c are illustrations of additional examples of a cartridge assembly for a medical material delivery device constructed in accordance with the principles of the present invention;

FIGS. 6a-c illustrate examples of dispensing elements of a medical material delivery device constructed in accordance with the principles of the present invention;

DETAILED DESCRIPTION OF THE INVENTION

Figure 1:
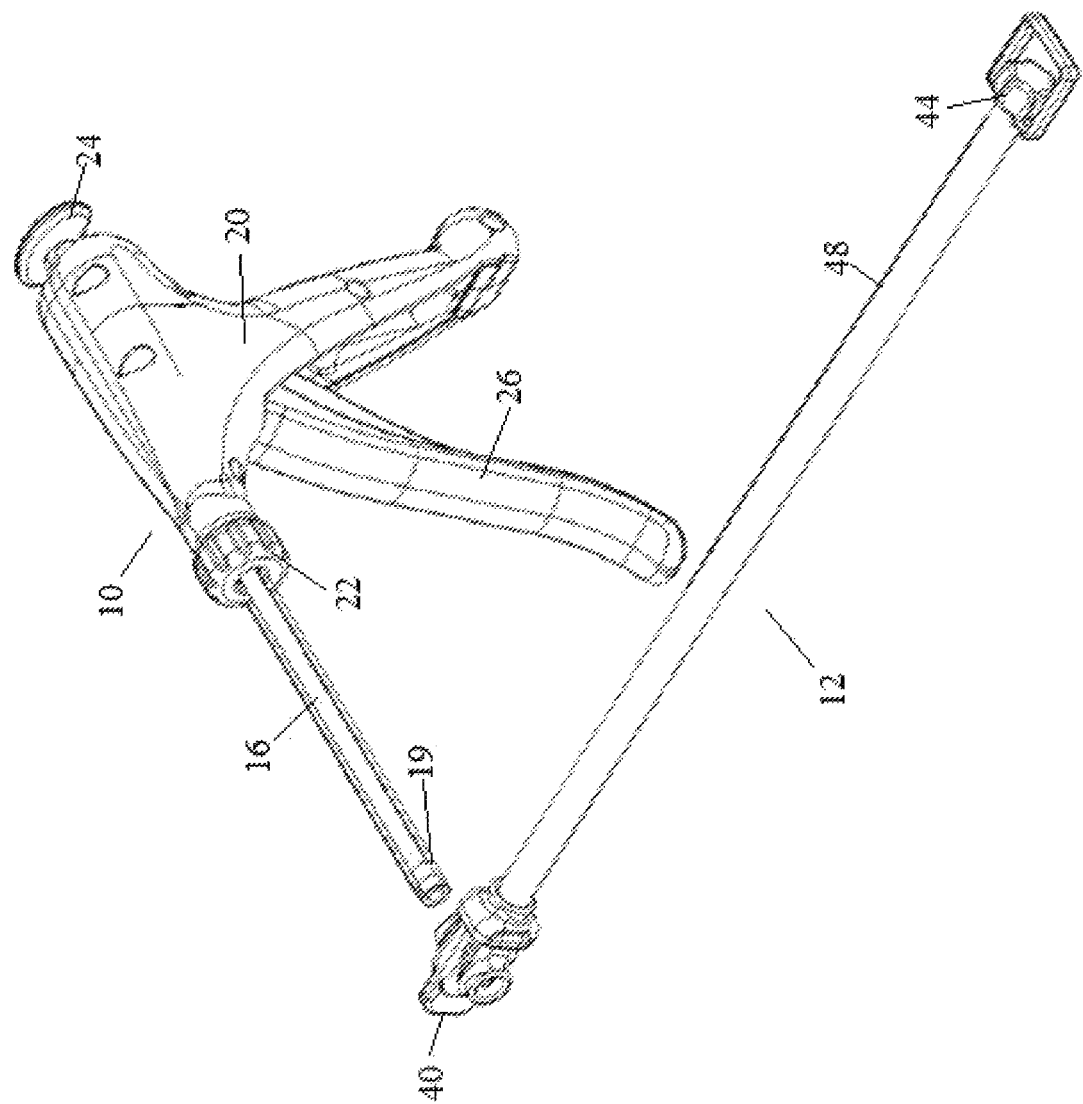
FIG. 1 is an illustration of an example of a biologic delivery system constructed in accordance with the principles of the present invention.
Figure 2:
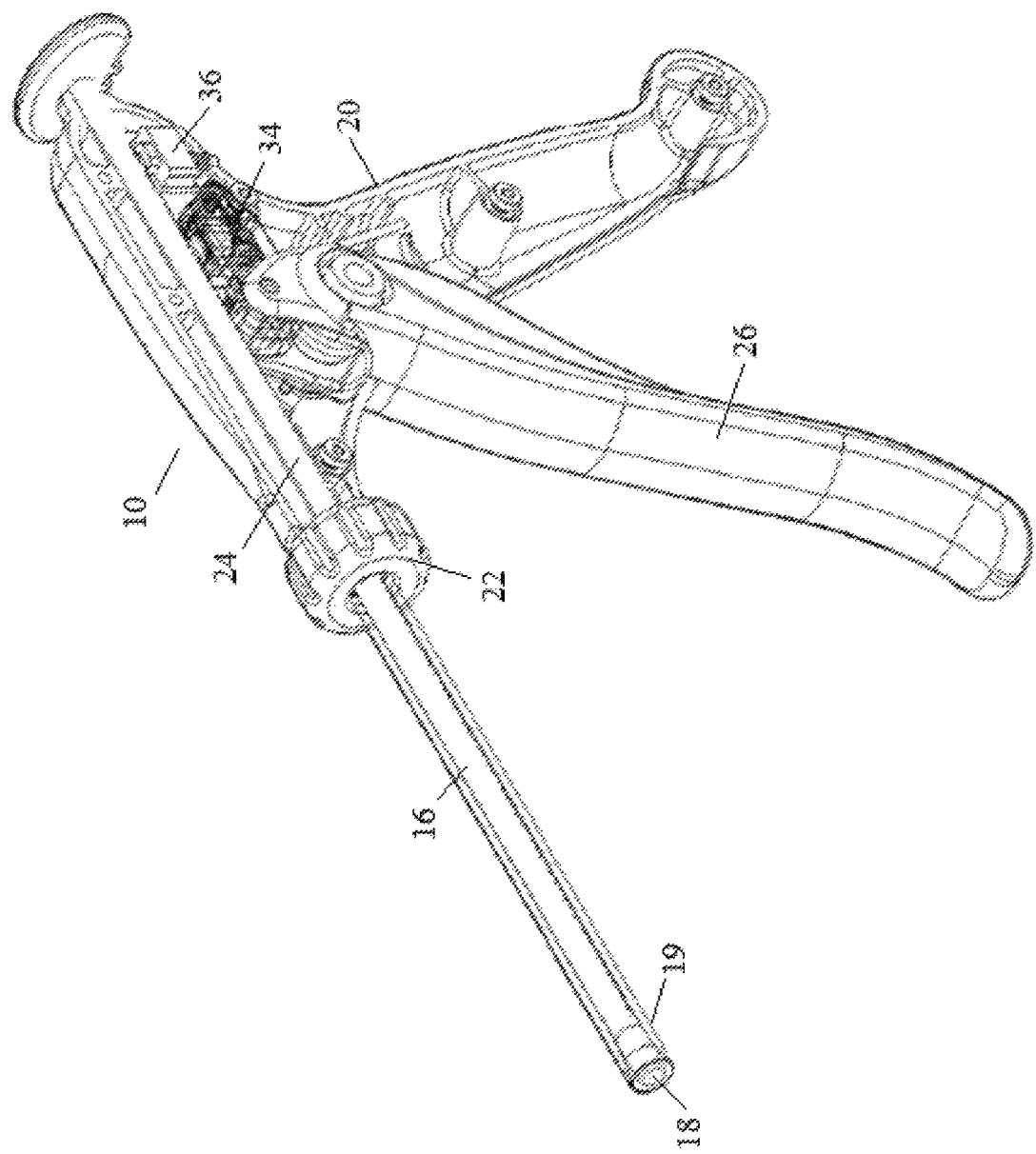
FIG. 2 is an illustration of an example of a medical material delivery device of the biologic delivery system shown in FIG. 1.
Figure 3:
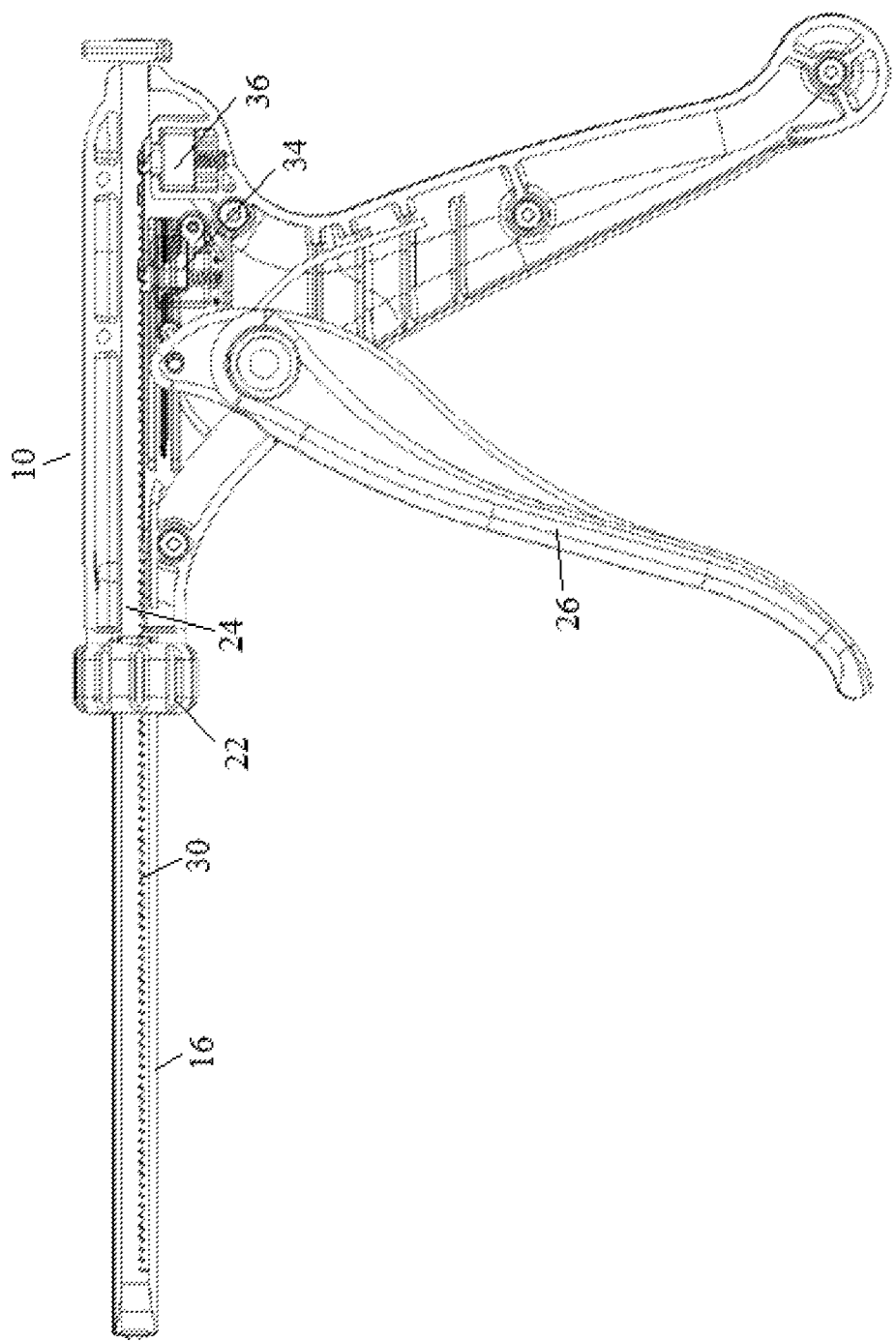
FIG. 3 is another illustration of the medical material delivery device shown in FIG. 3.
Figure 4:
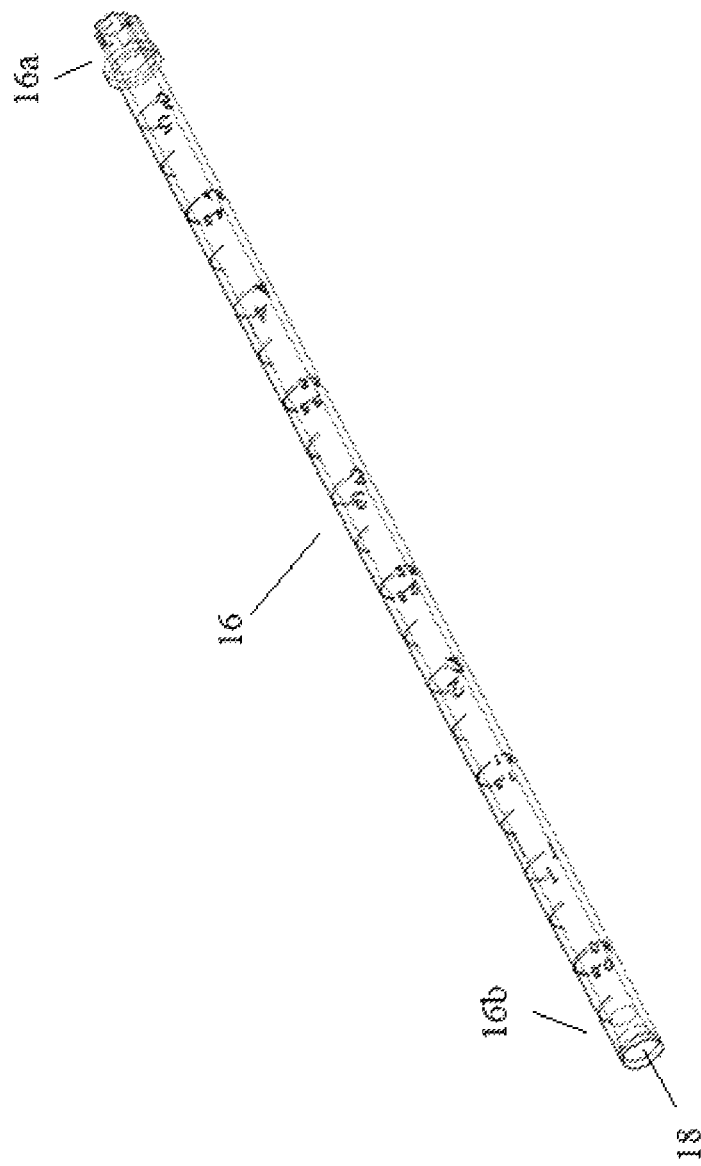
FIG. 4 is an illustration of an example of a cartridge for a medical material delivery device constructed in accordance with the principles of the present invention.

The present disclosure provides systems and methods of use thereof for preparing and delivering or dispensing biological, pharmaceutical, or other therapeutic or medical materials. In a particular example, the systems and methods of use described herein may include the preparation and delivery of bone graft materials or compounds to an orthopedic and/or spinal implant and/or surgical site.

Referring now to the drawing figures in which like reference designations refer to like elements, examples of a medical material delivery device 10 and an implant preparation assembly 12 and features and components thereof are shown in FIGS. 1-8, while an example of a compound preparation and packing assembly 14 is illustrated in FIGS. 9-15.

Now referring to FIGS. 1-4, the medical material delivery device 10 generally includes a selectively controllable mechanism to accurately dispense desired amounts of a prepared compound, specimen, and/or other medical materials from a loaded, elongate cartridge 16 to an implant or tissue site. The cartridge 16 may generally include an elongated tubular body having a proximal end 16a and distal end 16b, where the cartridge 16 defines a cavity or lumen 18 therein where a prepared compound, specimen, and/or other medical materials are stored prior to dispensing and use. The proximal end 16a of the cartridge 16 may include one or more features facilitating releasable engagement or selective interlocking with the device 10, which may include, for example, one or more ridges, grooves, or other surface features. The distal end 16b of the cartridge 18 may include or define a tapered wall thickness, as described further herein, to facilitate loading and/or expulsion of a medical material.

The length and/or lumen diameter of the cartridge 16 may vary depending on a particular desired use. In one example, dimensions of the cartridge 16 may be sufficient to store between approximately 2 cc and approximately 20 cc of a prepared compound. The cartridge may have a length between approximately 9 cm and approximately 50 cm, an inner diameter between approximately 0.4 cm and approximately 0.6 cm, and may have an outer diameter between approximately 0.6 cm and approximately 0.9 cm to facilitate navigating the cartridge into small areas or regions proximate to implants or other tissue structures. The cartridge 16 may include one or more measurement or volumetric labels or indicators to assist in loading and/or dispensing a desired amount of a medical material.

The cartridge 16 may be flexible and/or malleable to take on varying shapes or configurations to facilitate use of the device 10. For example, though illustrated as a substantially linear, straightened conduit, the cartridge 16 may be arcuate along one or more portions of its length. Varying degrees of curvature may be implemented to facilitate entry and positioning into small surgical spaces. In addition, a plurality of selectable delivery conduits may be provided with the device 10 to enable its use in a variety of different surgical sites having varying dimensions or tortuous routes leading to region where the graft or tissue material is desired. The cartridge 16 may further be constructed of a transparent or translucent material to allow visual confirmation and monitoring of graft material or other medical compound(s) traveling down the cartridge 16 and towards the delivery area. Opaque metal cartridges may be required as well when high pressure propagation of graft material is required (i.e. dry, highly morselized, almost atomized material). In this case the cartridge may have a high polish internal passage to mitigate frictional resistance when graft material of this kind is being translated outward through the cartridge.

The device 10 may provide a directional opening or outlet to disperse materials in a desired direction or orientation upon exiting the lumen 18 of the cartridge 16. For example, in the example shown in FIG. 5a, a distal tip accessory 19 may provide a tapered or curved opening directing material out of the lumen 18 in one or more pre-selected directions with respect to a longitudinal axis of the cartridge 16. The distal tip accessory 19 may have a myriad of different shapes and sizes to deliver the biological material to a surgical site which may include, for example, one or more implanted prostheses having cavities or regions therein for receiving the material. Particular examples of distal tip geometry may include funneled or tapered diameter tips; a dispersion port having a rectangular or square-like cross section; and/or angled bend or directional curve forming an angle with respect to a longitudinal axis of the cartridge 16. The distal tip 19 may also be steerable through the use of one or more steering wires, cables, or other controllably deflectable mechanisms.

Figure 5A:
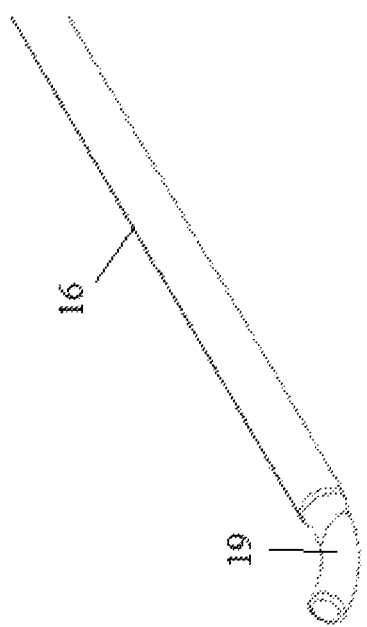
Figure 5B:
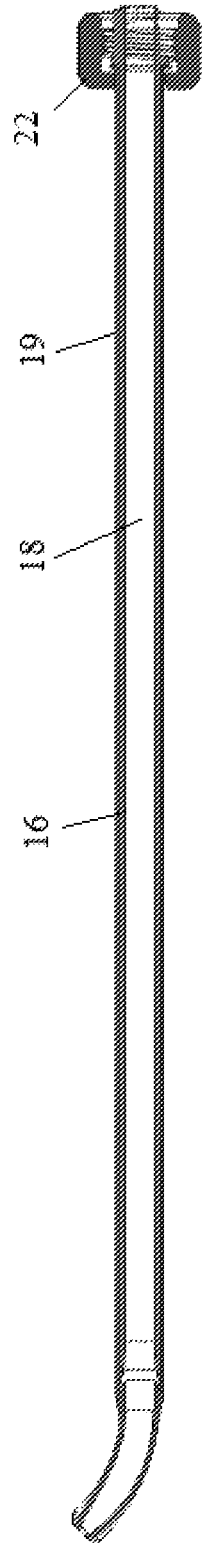

The distal tip accessory 19 may be coupled to the device 10 and/or the cartridge in a variety of different ways. For example, distal tip accessory 19 may couple directly to the distal end of the cartridge 16 in a cap or plug-like fashion, employing a friction fit and/or other releasably securable attachment mechanisms. In an alternative example, the distal tip accessory 19 may include a tapered or curved opening/spout and an elongated body that sheaths or covers substantially the entire length of the exterior of the cartridge 16, and is engageable directly to or with other portions of the device 10 (such as the device body 20 and/or locking element 22, described below) as shown in FIGS. 5b-5c.

The delivery device 10 may include a housing or device body 20 and an actuation mechanism attached to and/or contained therein to controllably dispense material from the lumen 18 of the cartridge 16. The proximal end 16a of the cartridge 16 may releasably couple directly to the device body 20 to couple with and be operable with the actuation mechanism. The releasable engagement may be achieved through the matable interlocking of one or more complimentary features on an end of the cartridge 16 and may include a locking element 22, such as a locking nut or other mechanical fastener, to sufficiently secure the cartridge 16 to the device body 20 for subsequent use.

The actuation mechanism of the device 10 may include a dispensing element or plunger 24 movably positioned within the delivery device 10, and controllably movable into and out of the lumen 18 of an attached cartridge 16 for the controlled expulsion of a medical compound from the cartridge 16. The dispensing element 24 may include an elongated, flexible body or cable that is sized and/or shaped to function as a plunger within the lumen 18 of an attached cartridge 16. The dispensing element 24 may, for example, have a cylindrical shape and/or rounded cross section substantially similar to the cross section of the lumen 18 of the cartridge 16, as shown in FIG. 6a.

Now referring to FIGS. 6b-c, the dispensing element 24 may include one or more features to improve upon medical compound extraction and/or delivery processes. For example, as shown in FIG. 6b, the dispensing element 24 may include a groove or other cutout 24a in the exterior wall or diameter of the body at a distal region of the dispensing element. This groove or cutout 24a allows trapped gas and air to pass out of the cartridge 16 or otherwise collect in the groove 24a when the dispensing element 24 is pushing a medical material out of the cartridge. Such air pockets can form when a medical material includes a wet graft or other biological material.

In an alternative example, the dispensing element 24 may include one or more sealing elements 24b on or about the distal tip of the dispensing element, as shown in FIG. 6c. The sealing element(s) 24b on the dispensing element 24 allow the dispensing element 24 and the device 10 to be used in a syringe-like manner to extract biological or medical material, such as bone marrow or other biopsies for subsequent use.

The dispensing element 24 may be coupled to the actuation mechanism such that manipulation or operation of the actuation mechanism results in the controlled movement of the dispensing element 24 towards the cartridge 16. The dispensing element 24 then controllably proceeds into and through the lumen 18 of the cartridge 16 to move the loaded materials/compound out of the cartridge 16 and into the desired area. The actuation mechanism may be configured and operable to selectively move the dispensing element 24 from the housing or body 20 of the delivery device 10 into the lumen of the cartridge 16 in discrete length increments. For example, the actuation mechanism may include an actuation element 26 operably coupled to the device body 20. The actuation element 26 may include, for example, a depressible trigger. The actuation mechanism may further include a ratchet assembly 28 mechanically linking the actuation element 26 to the dispensing element 24 for the controlled movement thereof. The dispensing element 24 may include, for example, an elongate body having a plurality of depressions, teeth, or grooves 30 therein that matably couple to one or more components of the ratchet assembly 28. The ratchet assembly may include, for example, a spring-loaded shuttle 32 that engages the grooves 30 of the dispensing element 24, where the shuttle 32 moves forward longitudinally in response to operation of the actuation element 28, and then retracts towards the rear of the device body 20 to re-engage the grooves 30 of the dispensing element 24 for further forward advancement. The ratchet assembly 28 may further include another spring-loaded engagement element/backstop 34 that prevents rearward travel of the dispensing element 24. The grooves 30 on the dispensing element 24 may be axially aligned along a length of the dispensing element, such that rotation of the dispensing element disengages the grooves 30 from the ratchet mechanism, thereby allowing a physician to quickly retract or remove the dispensing element 24 from the device 10 (or alternatively, to push manually drive the dispensing element 24 forward and dispense material from the cartridge 16 independently of the ratchet mechanism). Such "quick-release" operation of the dispensing element 24 facilitates ease of use of the device 10 and enables timely exchanges and use of multiple cartridges in a single medical procedure.

Alternatively to the engaged grooves 30 and the ratchet assembly 28, the dispensing element 24 may be substantially smooth and may interact with the actuation mechanism through compression or friction to controllably move the dispensing element 24 as desired.

Figure 7:
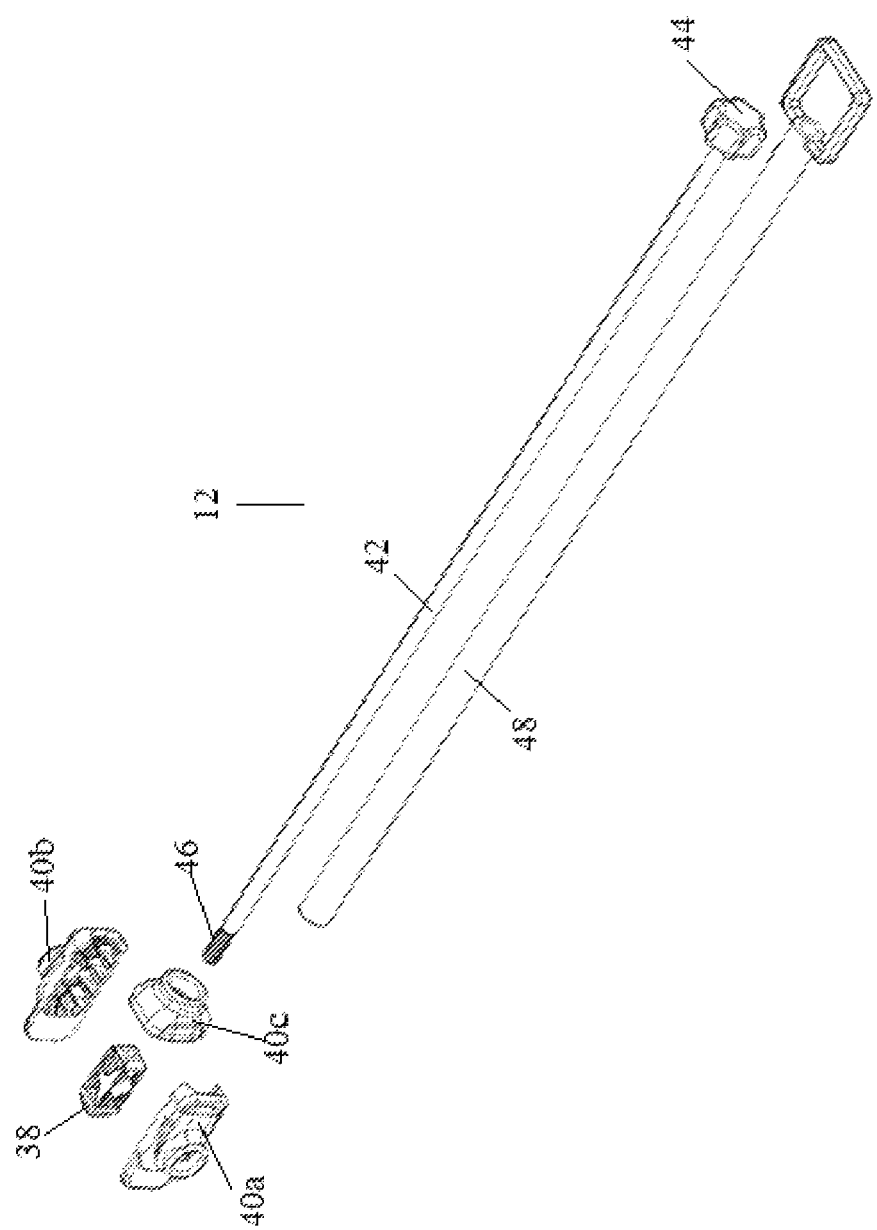
FIG. 7 is an illustration of an example of an implant preparation assembly constructed in accordance with the principles of the present invention.
Figure 8:
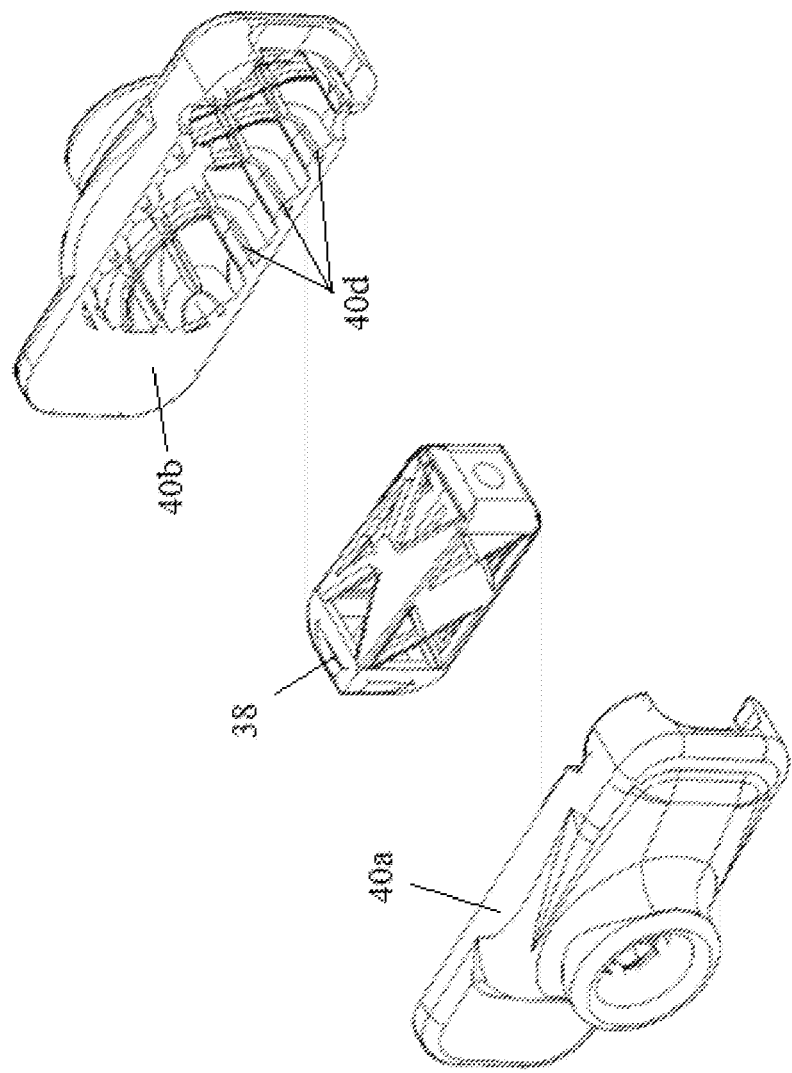
FIG. 8 is another illustration of components of the implant preparation assembly shown in FIG. 7.

Now referring to FIGS. 1 and 7-8, the implant preparation assembly 12 provides an improved mechanism by which to deliver biologic or other medical materials or compounds to an implant having a cage, lattice, or other structure intended for use with such medical compounds. For example, an implant 38 may be placed within an implant capsule 40, which may include one or more housing components 40, 40b, 40c that can be releasably assembled to define a cavity therein to receive and enclose the implant 38. The implant capsule 40 may include or define a plurality of ribs 40d on an interior surface thereof, which can aid in directing the medical material or compound into the crevices and structure of the implant 38.

The implant preparation assembly 12 may include an implant delivery instrument 42, which may include an elongate body having a knob or other control means 44 at a proximal end thereof, and an implant engagement feature 46 at a distal end thereof to releasably attach the implant delivery instrument 42 to the implant 38. The implant engagement feature 46 may include, for example, a threaded surface, a snap fit feature, or other releasable interlocking mechanism. The implant capsule 40 may include or define a pathway for the implant delivery instrument 42 to attach to a corresponding feature of the implant 38. For example, the implant capsule housing 40c may define an aperture therethrough of sufficient size to allow the implant delivery instrument 42 to pass therethrough and attach to a threaded surface or other complementing matable feature on the implant 38.

The implant preparation assembly 12 may include a delivery instrument sheath 48 that includes an elongate body with a lumen or passageway therethrough to receive at least a portion of the implant delivery instrument 42. The sheath 48 can ease or facilitate insertion of the implant 38 into a surgical site, and may further provide a locking or resistive surface at a distal end thereof so that the implant delivery instrument 42 can be disengaged from the implant 38 while substantially maintaining the implant 38 in the desired implanted position.

The cartridge 16 may be matable or engageable with the implant capsule 40 to deliver contents into an interior cavity or passage of the implant 38 to substantially fill the internal structure, lattice, and/or framework of the implant 38. For example, one or more portions of the capsule housing 40a and/or 40b may include a valve or other opening allowing the insertion of the distal end of the cartridge 16 therein, and subsequent operation of the delivery device 10 can inject the medical compound or material from the cartridge into the receiving portions of the implant 38. By substantially sealing the implant 38 within the implant capsule 40, the delivery of medical compound from the cartridge 16 can propagate throughout the structure of the implant 38 in a substantially uniform way under a desired amount of pressure, and fill small spaces or regions of the implant 38 that might otherwise be inaccessible using traditional compound packing methods (e.g., using small spatulas to fill an implant). Moreover, the encapsulation of the implant 38 avoids overflow or leakage of delivered material to the implant 38, which can reduce waste and associated cost of the medical materials.

The systems and methods used herein may be utilized with various medical compounds deliverable through the cartridge 16. A particular cartridge 16 may be pre-loaded with a compound, such as processed bone graft material from a tissue bank, and provided to a physician read for use. In other situations, however, a physician may desire the use of autograft materials that must be prepared and positioned within the cartridge in an operating room environment and/or during a procedure.

Figure 9:
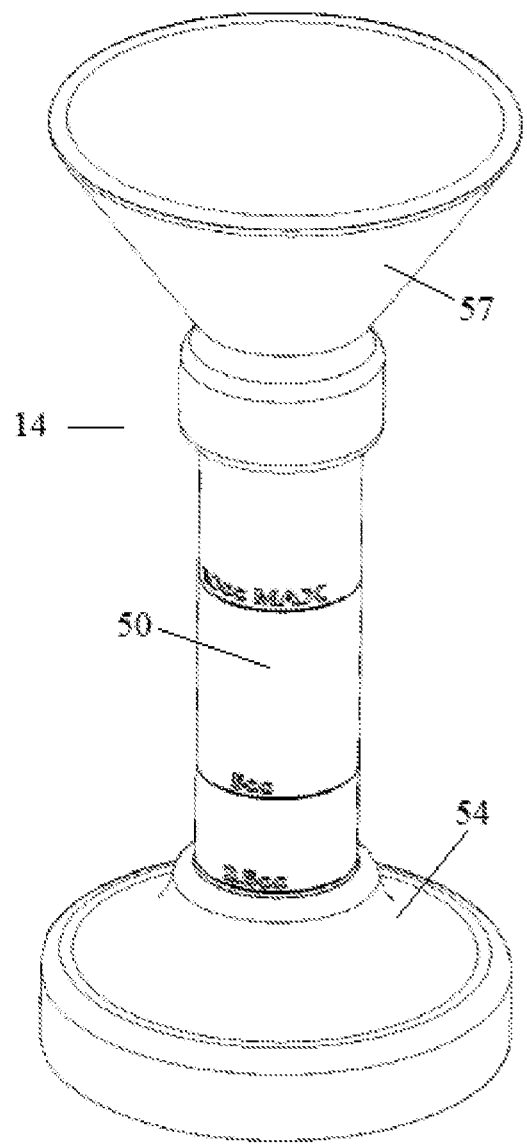
FIG. 9 is an illustration of an example of a compound preparation and packing assembly constructed in accordance with the principles of the present invention.
Figure 10:
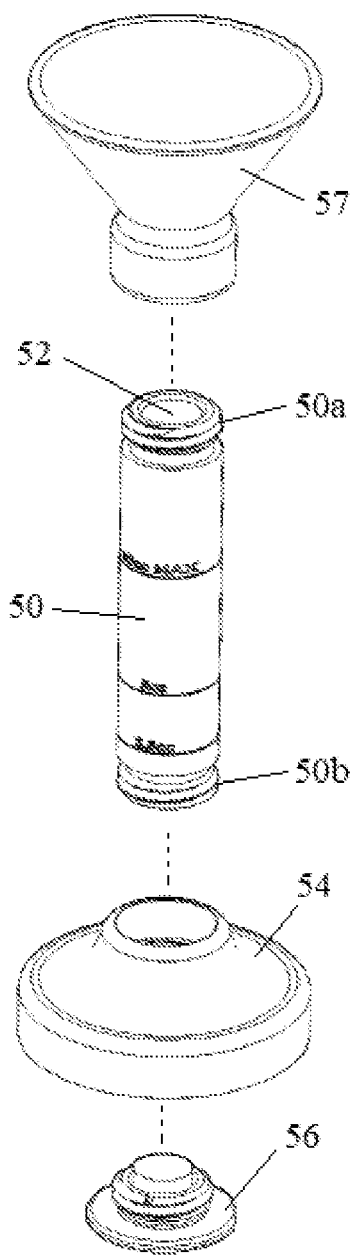
FIG. 10 is an exploded assembly view of the compound preparation and packing assembly shown in FIG. 9.

Now referring to FIGS. 9-15, an example of a compound preparation and packing assembly 14 for such uses is illustrated that improves loading and retention of a mixed medical compound into the cartridge 16. As shown in FIGS. 9-10, the assembly 14 may generally include a primary container or receptacle 50 defining a cavity 52 therein for receiving a mixed medical compound. The receptacle 52 may include a substantially tubular or cylindrical body, and the cavity 52 may comprise a substantially cylindrical lumen or passageway extending through all or a portion of the receptacle 50. The cavity 50 may be accessible through one or more openings in the receptacle (for example, the cavity 50 may form a first opening at one end 50a of the receptacle 50 and a second opening at an opposite end 50b of the receptacle 50). The receptacle 50 may be sized and shaped to accommodate a desired volume of a medical compound. For example, the receptacle 50 may be sized such that the cavity 52 has a volume between approximately 2 cc and approximately 10 cc. The receptacle may have a length between approximately 1 cm and approximately 15 cm, an inner diameter between approximately 1 cm and approximately 2 cm, and may have an outer diameter between approximately 1 cm and approximately 3 cm to accommodate and provide the other features disclosed herein. The receptacle 50 may include one or more measurement or volumetric labels or indicators to assist in allocating a desired amount of a medical material for use.

A base 54 and a cap 56 may be included in the assembly 14 to releasably attach to the receptacle 50 to cover or close access points or openings to the cavity 52. The base 54 may releasably engage to the receptacle 50 through a threaded surface on the end 50b of the receptacle 50, and provide an expanded diameter or size to stabilize and allow the assembly 14 to remain upright during use. The cap 56 may releasably engage to the end 50b of the receptacle 50 and/or the base 54 through a threaded surface or other selectively interlocking mechanism.

The cap 56 may define one or more vents 56a disposed therein to capture a release of gas or other pressure from an interior of the cavity 52 when the cap 56 is loosened or partially retracted from the base 56 and/or receptacle 50. The vents 56a may be radially disposed about a circumference of the cap 56, and have a diameter similar to that of the interior cavity 52 of the receptacle 50 to depressurize or otherwise receive a portion of material or gas escaping the cavity 52.

The assembly 14 may include a funnel 57 releasably engageable to the receptacle 50 to aid in directing a medical material or compound into the cavity 52 of the receptacle 50. The releasable engagement may be achieved through a threaded surface or other selectively interlocking mechanism at the first end 50a of the receptacle 50.

Figure 11:
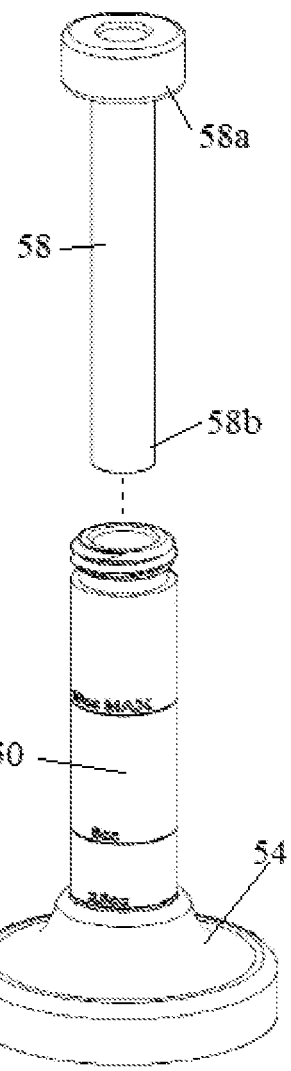
FIG. 11 is another illustration of an example of a compound preparation and packing assembly constructed in accordance with the principles of the present invention.
Figure 12:
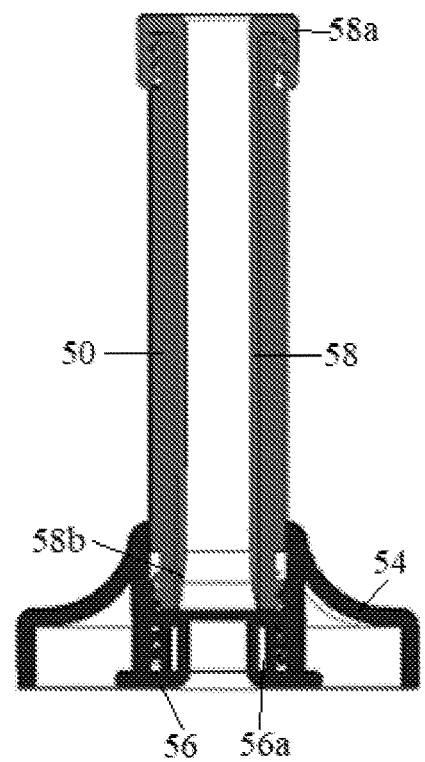
FIG. 12 is a cross-sectional view of the assembled example of the compound preparation and packing assembly shown in FIG. 11.

Now referring to FIGS. 11-12, the assembly 14 may include a first tube 58 that is sized and shaped to be slidably positioned with the cavity 52 of the receptacle 50. The first tube 58 may define a generally cylindrical body with a lumen or passageway extending therethrough. The first tube 58 may be sized and shaped to fit within the cavity 52 of the receptacle 50 with marginal to substantially no space existing between an outer diameter of the first tube 58 and an inner wall or dimeter of the cavity 52. The first tube 58 may define a proximal end 58a that is releasably engageable with the receptacle 50 (for example, via a threaded interlock at the first end 50a of the receptacle), and the first tube 58 may define a distal end 58b having a tapered wall thickness.

Figure 13A:
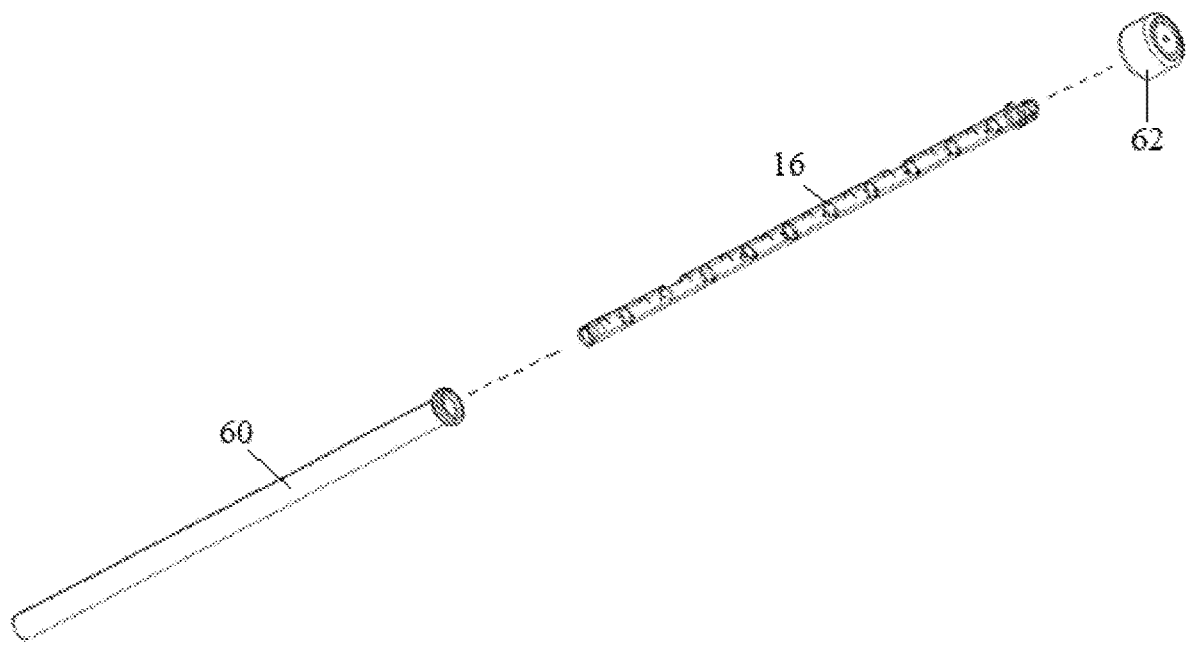
FIGS. 13a-c illustrate components of an example of a compound preparation and packing assembly constructed in accordance with the principles of the present invention.

Now referring to FIG. 13a, the assembly 14 may include a second tube 60 that is sized and shaped to be slidably positioned with the first tube 58. The second tube 60 may define a generally cylindrical body with a lumen or passageway extending therethrough sized and shaped to slidably receive the cartridge 16 therein with marginal to substantially no space existing between an outer diameter of the cartridge 16 and an inner wall or dimeter of the passageway or lumen of the second tube 60. The second tube 60 may be sized and shaped to fit within the lumen or passage of the first tube 58 with marginal to substantially no space existing between an outer diameter of the second tube 60 and an inner wall or dimeter of the passage or lumen of the first tube 58.

Figure 13B:
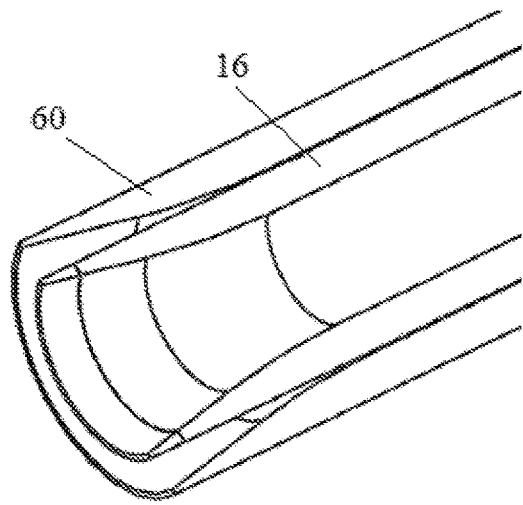

The second tube 60 and the cartridge 16 may be longitudinally positioned with respect to each other such that a distal end of the cartridge is substantially aligned with a distal end of the second tube 60, an example of which is illustrated in the cross-sectional view of FIG. 13b. Having the distal end and opening of the cartridge 16 substantially coincident or adjacent the distal end and opening of the second tube 60 may be used when a medical material or compound having a high degree of flowability or reduced density is being used and loaded into the cartridge 16 (as described in more detail below). A flowable medical material would be more able to traverse larger decreases in diameter between the receptacle 50, respective tubes 58, 60, and cartridge 16.

Figure 13C:
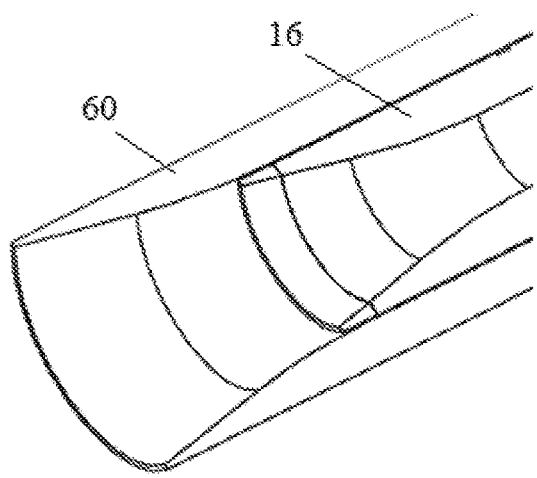
Figure 14:
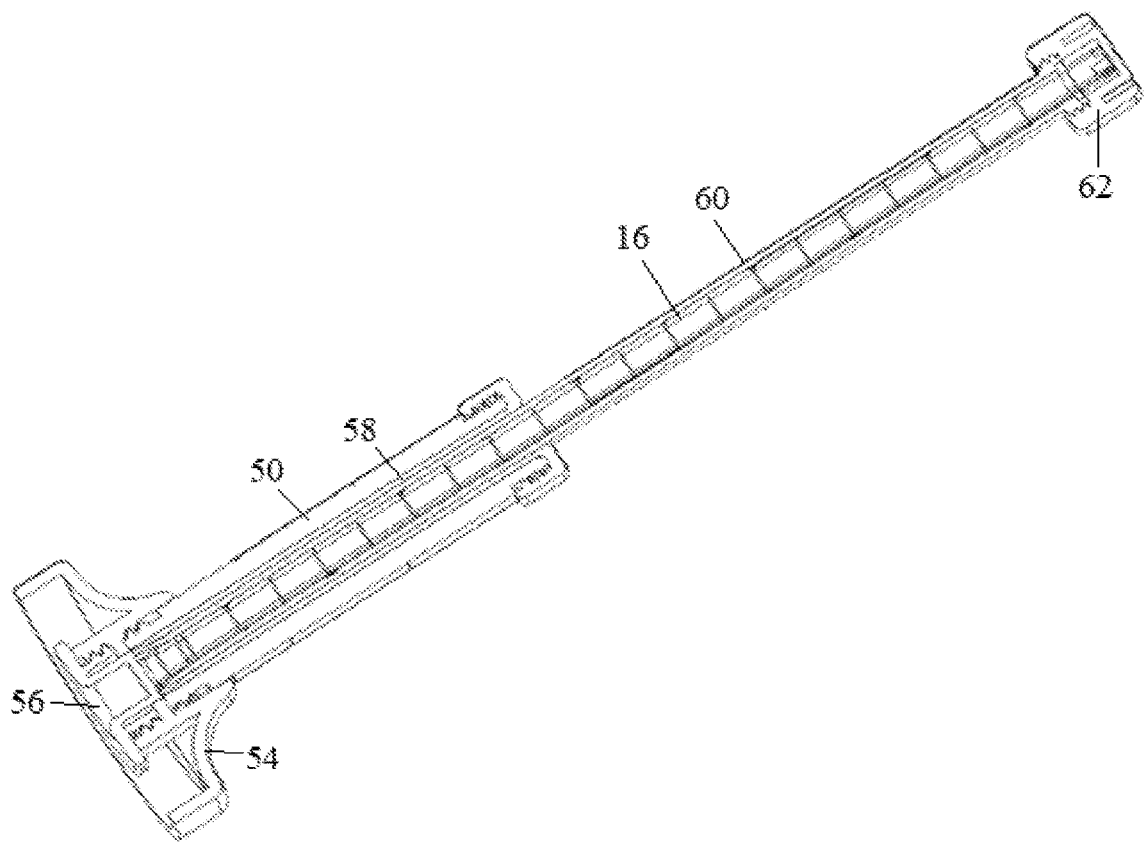
FIG. 14 is a cross-sectional view of an example of a compound preparation and packing assembly constructed in accordance with the principles of the present invention.
Figure 15:
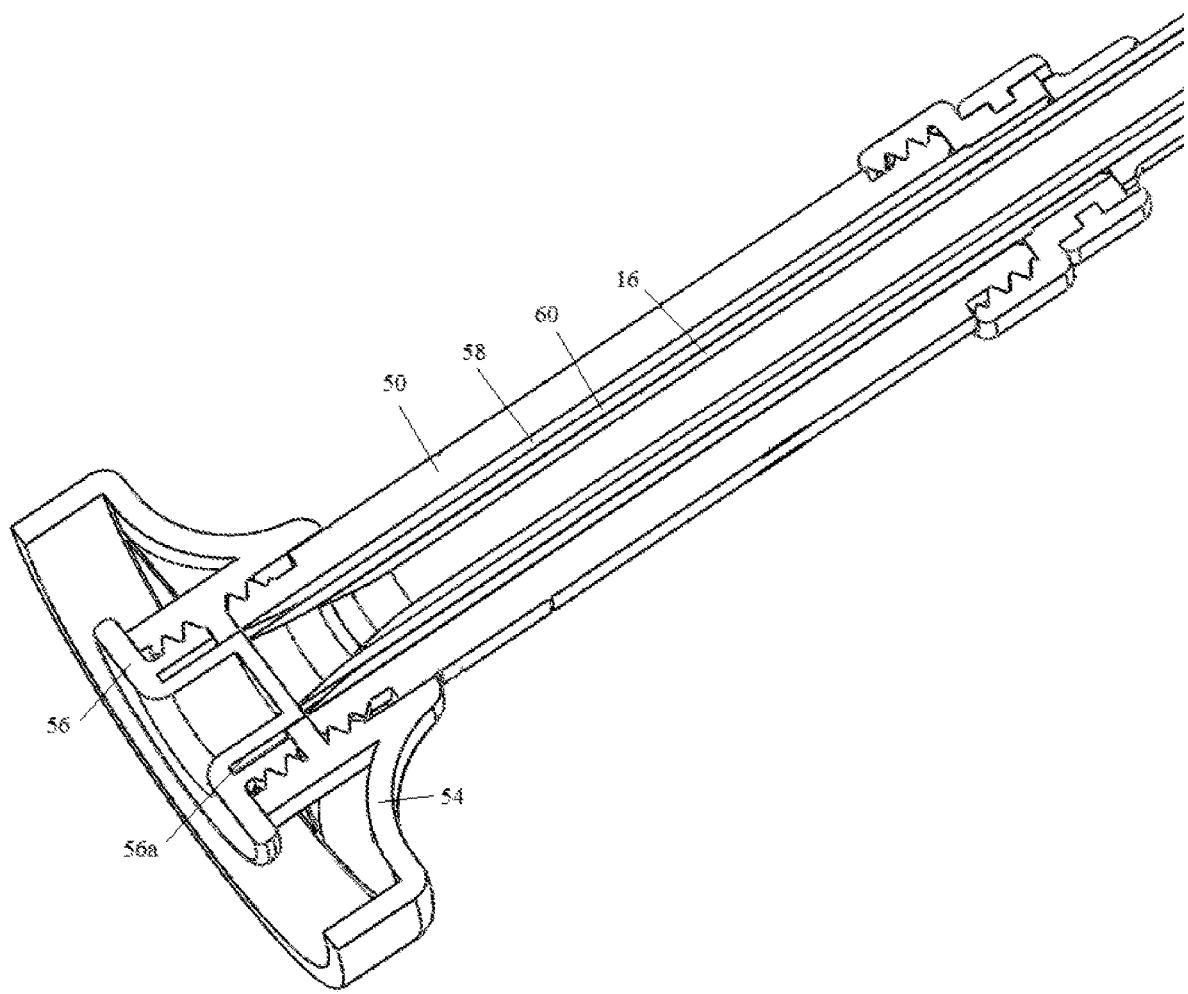
FIG. 15 is a closer cross-sectional view of the compound preparation and packing assembly of FIG. 14.

In alternative arrangement, the second tube 60 and the cartridge 16 may be longitudinally positioned with respect to each other such that a distal end of the cartridge 16 is longitudinally offset from a distal end of the second tube 60, an example of which is illustrated in the cross-sectional view of FIG. 13c. Having the distal end and opening of the cartridge 16 substantially offset from the distal end and opening of the second tube 60 aligns the respective tapering of the ends of the second tube 60 and the cartridge 16 to form a single, substantially continuous tapered or funneled surface leading into the interior lumen 18 of the cartridge. This configuration may be beneficial when a less flowable medical material having a greater density is being used and loaded into the cartridge 16 (as described in more detail below).

The longitudinal positioning between the second tube 60 and the cartridge 16 may be achieved in a variety of different ways, including but not limited to employing one or more removable spacers on or about the cartridge 16 and/or second tube 60, a telescoping mechanism, providing a selection of multiple cartridges and second tubes having varying set lengths, and/or other length augmenting components or features.

A cap 62 may be releasably engageable with the second tube 60 to securely enclose the cartridge within the interior of the second tube 60. The cap 62 may define a threaded surface or have other matable interlocking features to attach to the second tube 60. The cap 62 may be constructed from a force absorbing material, such as rubber, santoprene, polyethylene, polypropylene, or the like to allow a physician to exert force on the cap 62 without resultant damage to the cartridge 16.

In an exemplary use of the compound preparation and packing assembly 14, a medical compound, mixture, or other biological material may be placed into the cavity 52 of the receptacle 50. The receptacle 50 may be coupled to the base 54 and the cap 56, while the material may be placed into the cavity 52 using the funnel 57 through the opposite end or opening 50a. Once sufficient material has been loaded into the receptacle 50, the funnel 57 may be removed, and the first tube 58 may then be slidably inserted into the cavity 52 and maneuvered downward towards a bottom edge or segment of the cavity 52. Insertion of the tapered distal end 58b into the cavity 52 of the receptacle 50 will cause the medical material to transition into and upward the internal lumen or passage of the first tube 58. The first tube 58 may be secured to the receptacle through the releasably engagement coupling at the proximal end 58a of the first tube 58. Securing the first tube 58 to the receptacle 60 ensures that the first tube 58 is not ejected or pushed out of the receptacle 50 due to imparted forces experienced with the subsequent insertion of the second tube 60, as described below.

The cartridge 16 may then be placed at least partially inside the interior of the second tube 60, and the cap 62 may be secured to the second tube 60 to secure the assembly of these components together. The second tube 60 (now containing the cartridge 16) may then be slidably inserted into the first tube 58, and maneuvered downward towards a bottom edge or segment of the first tube 58. Insertion of the tapered distal ends of the second tube 60 and/or the cartridge 16 into the passage of the first tube 58 will cause the medical material to transition into and upward the internal lumen 18 of the cartridge 16.

Should additional force be needed to drive the second tube 60 and/or cartridge 16 downward further into the receptacle 50, a physician could use a mallet or other striking took to apply force to the impact-absorbing cap 62. Such additional force may be needed when the medical material is very finely granulated such that is partially solidifies together under moderate pressure. In addition and/or alternatively to striking the cap 62, the cap 56 on an underside of the base 54 and receptacle 50 may be opened or retracted to provide additional space for the medical material (e.g., by effectively expanding the longitudinal length of the cavity 52) and/or to allow the medical material to decompress somewhat to ease loading the cartridge 16.

Once the cartridge 16 has been loaded with the desired amount of medical material, the second tube 60 and the cartridge 16 may be removed from the receptacle 50, and the cartridge 16 may be attached to the medical device 10 for subsequent dispensing of the medical material into an implant and/or surgical site.

The described method to prepare and package the medical material into the cartridge 16 provides an atraumatic way to place the medical material into the cartridge while avoiding damaging the cells or other biological features of a particular compound being use, and also reduces the likelihood of spillage or other waste that may arise from traditional packing methods.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. A medical compound preparation and delivery system, comprising:
   a delivery device, the device including a depressible trigger operably coupled to move a plunger;
   a cartridge releasably coupled to the delivery device, the cartridge defining a lumen therethrough to receive at least a portion of the plunger therein;
   a receptacle defining a cavity therein for receiving a medical compound;
   a first tube slidably positionable within the cavity of the receptacle; and
   a second tube slidably positionable within the first tube, wherein the cartridge is slidably positionable within the second tube.

2. The system of claim 1, wherein the cavity of the receptacle is substantially cylindrical.

3. The system of claim 1, wherein the cavity extends entirely through the receptacle, and wherein the system further comprises a base removably coupled to the receptacle to cover a portion of the cavity.

4. The system of claim 1, wherein the cartridge defines an elongated substantially tubular body.

5. The system of claim 4, wherein the cartridge includes an arcuate tip.

6. The system of claim 1, wherein the delivery device includes a ratchet mechanism engageable with the plunger.

7. The system of claim 1, wherein the delivery device includes a locking element configured to secure the cartridge to the delivery device.

8. The system of claim 1, wherein the cavity of the receptacle has a volume between approximately 2 cc and approximately 20 cc.

9. The system of claim 1, wherein the lumen of the cartridge defines a volume between approximately 2 cc and approximately 20 cc.

10. The system of claim 1, wherein the plunger defines a groove at a distal end thereof.

11. The system of claim 1, wherein the plunger includes a sealing element at a distal end thereof.

12. The system of claim 1, wherein each of the cartridge, first tube, and second tube define a tapered end.

13. The system of claim 1, further comprising a base that is releasably engageable with the receptacle.

14. The system of claim 13, further comprising a cap that is releasably engageable with the base.

15. The system of claim 1, further comprising a distal tip accessory that defines a curved spout, wherein the distal tip accessory is releasably engageable with the delivery device to substantially enclose the cartridge therein.

16. A method of preparing a medical compound for delivery, comprising:

placing a medical compound into a cavity of a receptacle;

slidably positioning a first tube into the cavity such that the medical compound is moved into the first tube;

slidably positioning a second tube into the first tube such that the medical compound is moved into the second tube;

slidably positioning a cartridge into the second tube such that the medical compound is moved into the cartridge; and releasably securing the cartridge to a delivery device, wherein the delivery device includes a depressible trigger operably coupled to move a plunger into the cartridge to controllably dispense the medical compound from the cartridge.

17. The method of claim 16, wherein the medical compound includes bone graft.

18. The method of claim 16, wherein the receptacle includes a substantially cylindrical body.

19. The method of claim 16, wherein the delivery device includes a ratchet mechanism engageable with the plunger.

20. The method of claim 16, wherein the delivery device includes a locking element configured to secure the cartridge to the delivery device.

* * * * *